US012672785B2

(12) United States Patent
Zhang et al.

(10) Patent No.: US 12,672,785 B2
(45) Date of Patent: Jul. 7, 2026

(54) METHOD AND APPARATUS FOR OBTAINING RELEVANT CHARACTERISTIC PARAMETERS AND INDEXES OF TONOARTERIOGRAM (TAG) SIGNALS

(71) Applicant: Hong Kong Centre for Cerebro-Cardiovascular Health Engineering Limited, Hong (HK)

(72) Inventors: Yuanting Zhang, Hong Kong (HK); Nan Ji, Hong Kong (HK); Ting Xiang, Hong Kong (HK)

( * ) Notice: Subject to any disclaimer, the term of this patent is extended or adjusted under 35 U.S.C. 154(b) by 880 days.

(21) Appl. No.: 17/520,639

(22) Filed: Nov. 6, 2021

(65) Prior Publication Data

US 2023/0068873 A1    Mar. 2, 2023

(30) Foreign Application Priority Data

Jul. 27, 2021    (CN) .......................... 202110850045.8

(51) Int. Cl.
A61B 5/00          (2006.01)
A61B 5/02          (2006.01)
(Continued)

(52) U.S. Cl.
CPC ...... A61B 5/02108 (2013.01); A61B 5/02007 (2013.01); A61B 5/02416 (2013.01); (Continued)

(58) Field of Classification Search
None
See application file for complete search history.

(56) References Cited

U.S. PATENT DOCUMENTS 5,152,297 A * 10/1992 Meister .................. A61B 5/022
600/485
2012/0157791 A1* 6/2012 Hersh .................... A61B 5/725
600/301
(Continued)

*Primary Examiner* — Tse W Chen
*Assistant Examiner* — Martin Nathan Ortega
(74) *Attorney, Agent, or Firm* — NCC-IP; Nevin Stuart Carmichael

(57) ABSTRACT

The present invention provides a method and an apparatus for obtaining relevant characteristic parameters and indexes of tonoarteriogram (TAG) signals, relating to the technical field of blood pressure monitoring. A signal acquisition module acquires TAG signals from a target subject; a signal processing module obtains relevant characteristic parameters and indexes of continuous blood pressure from obtained TAG signals of target subject by calculating and processing through a predetermined mathematical model and a statistical algorithm, wherein the relevant characteristic parameters and indexes of continuous blood pressure include at least one of root mean square value of continuous blood pressure (RMSBP) and standard deviation of continuous blood pressure (SDBP), an evaluation module evaluates the status of continuous blood pressure based on characteristic parameters and indexes obtained from the target subject, an alarm module initiates an alarm when the relevant characteristic parameters and indexes of continuous blood pressure monitored to be abnormal, which allows to monitor the blood pressure of the target user at different period of time, realizing rapid blood pressure measurement, and enabling timely alarms to ensure the safety of the target user.

11 Claims, 7 Drawing Sheets

(51) Int. Cl.
  *A61B 5/021*    (2006.01)
  *A61B 5/024*    (2006.01)
  *A61B 5/318*    (2021.01)

(52) U.S. Cl.
  CPC ............ *A61B 5/318* (2021.01); *A61B 5/6805*
        (2013.01); *A61B 5/681* (2013.01); *A61B*
        *5/6898* (2013.01); *A61B 5/746* (2013.01);
        *A61B 2560/0209* (2013.01); *A61B 2562/0247*
                          (2013.01)

(56)                 References Cited

U.S. PATENT DOCUMENTS

| | | | | |
|---|---|---|---|---|
| 2013/0172759 A1* | 7/2013 | Melker | .................. | A61B 5/682 |
| | | | | 600/476 |
| 2013/0324855 A1* | 12/2013 | Lisogurski | ............ | A61B 5/318 |
| | | | | 600/476 |
| 2018/0333106 A1* | 11/2018 | Roberts | .................. | G16H 50/30 |
| 2019/0150851 A1* | 5/2019 | Clark | ........................ | A61B 5/42 |
| 2020/0253562 A1* | 8/2020 | Newberry | ................ | A61B 5/01 |
| 2021/0000347 A1* | 1/2021 | Stump | .................. | A61B 5/1102 |
| 2021/0244302 A1* | 8/2021 | Lizio | ..................... | A61B 5/7239 |
| 2024/0307000 A1* | 9/2024 | Ferber | ................. | A61B 5/7275 |

* cited by examiner

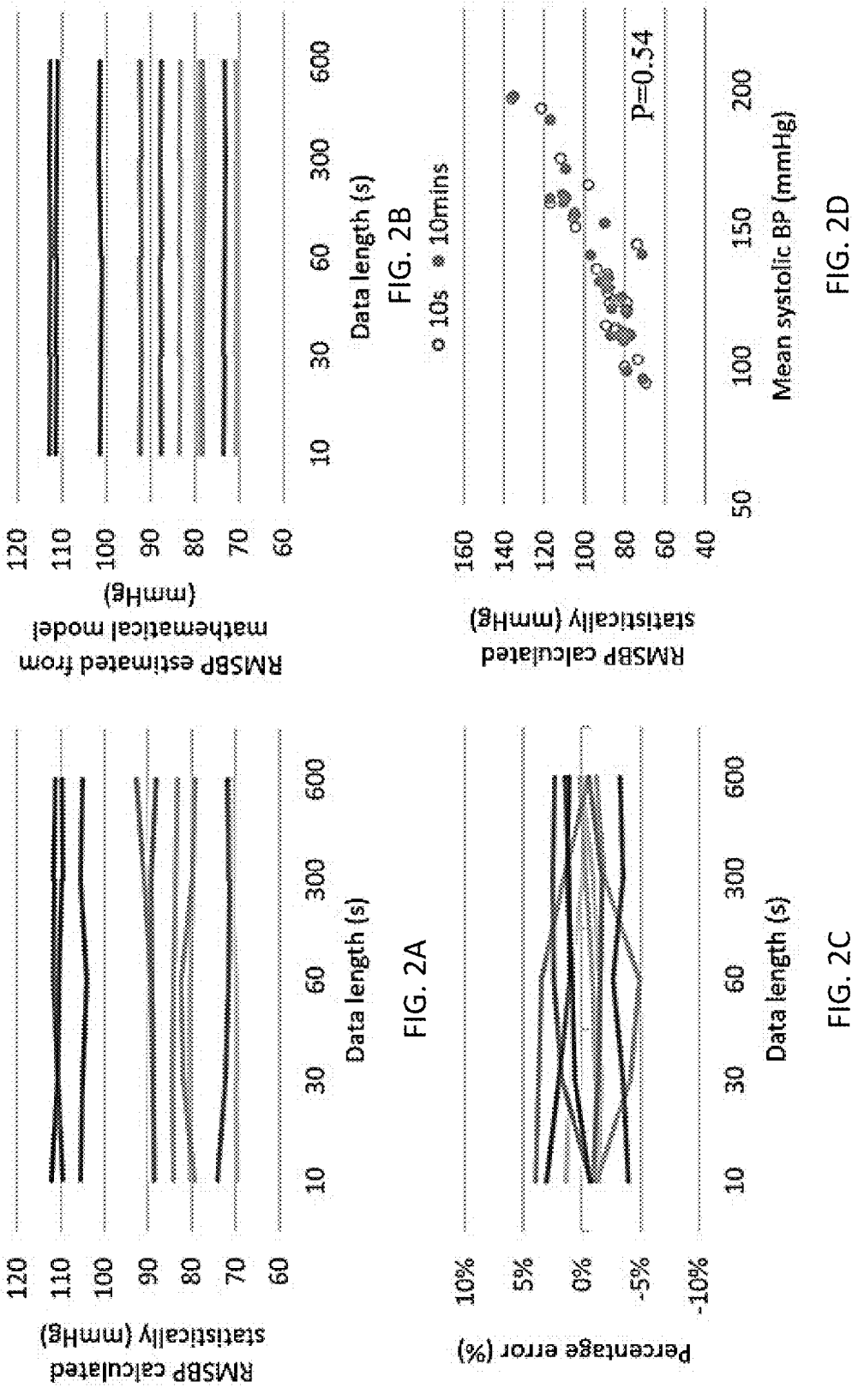

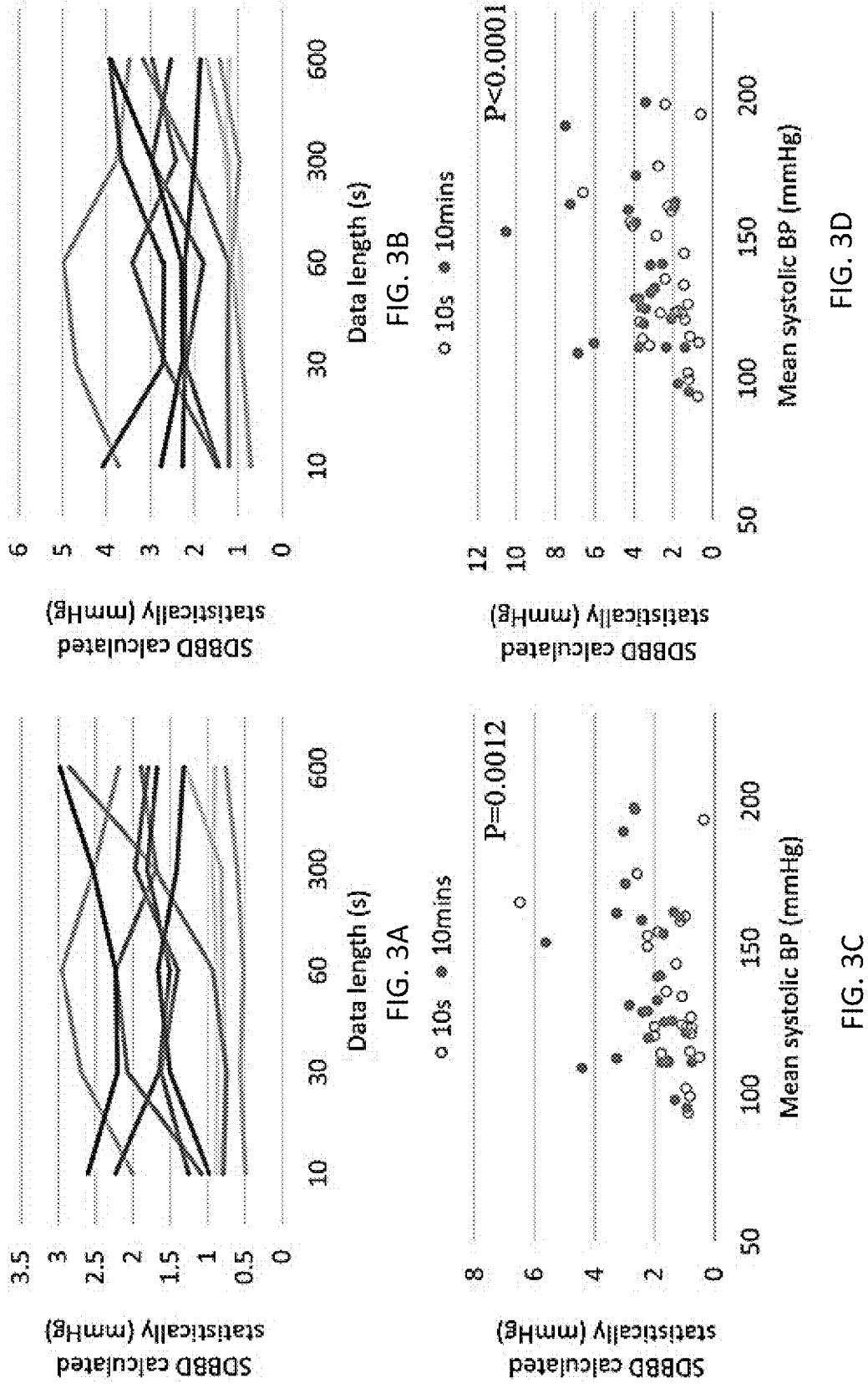

METHOD AND APPARATUS FOR OBTAINING RELEVANT CHARACTERISTIC PARAMETERS AND INDEXES OF TONOARTERIOGRAM (TAG) SIGNALS

FIELD OF THE INVENTION

The present application relates to the technical field of unobtrusive continuous blood pressure measurement, specifically, the application relates to a processing method and apparatus for obtaining relevant characteristic parameters and indexes of tonoarteriogram (TAG) signals.

BACKGROUND OF THE INVENTION

Blood pressure, as an important physiological parameter, is highly associated with a variety of diseases, especially cardiovascular and cerebrovascular diseases. Commonly used indicators to assess blood pressure include diastolic blood pressure, systolic blood pressure, pulse pressure, mean blood pressure, and diastolic/systolic blood pressure variability.

Blood pressure variability refers to the fluctuation of blood pressure over a certain period of time. An increase in blood pressure variability indicates the increase the shear force on the blood vessel wall, leading to the development of atherosclerosis and consequently to cardiovascular events. Blood pressure variability is usually expressed as the standard deviation or coefficient of variation of beat-to-beat diastolic/systolic blood pressure readings measured over a specific time period.

Tonoarteriogram (TAG) is defined as a graphical recording of the continuous arterial blood pressure signal as a function of time. TAG can be obtained by unobtrusive, wearable, or cuffless continuous arterial blood pressure measuring devices. For conventional snapshot and beat-to-beat blood pressure measurements, the metrics commonly used in the assessment are more than complete.

The cuffless, unobtrusive continuous blood pressure measurement or unobtrusive arterial TAG signal, differs from traditional snapshot and beat-to-beat blood pressure measurements, consists of a continuous blood pressure waveform per cardiac cycle, providing richer physiological information, including the traditional beat-to-beat systolic and diastolic blood pressure, but also blood pressure values in between, etc. TAG signal can be used for the assessment of the cardiovascular system and early diagnosis of disease. However, there are still no relevant characteristic parameters and methods for evaluating and analyzing the TAG signal.

In specific scenarios, such as for wearable and mobile health applications, there is a strong need for reliable ultra-short-term metric of continuous blood pressure to avoid motion artifacts and to meet the need for rapid diagnosis of acute cardiovascular disease. While both mid- and long-term methods for analyzing blood pressure variability have been extensively studied in data from normal and cardiac patients, there is a lack of research on more effective methods for assessing ultra-short-term and short-term blood pressure levels and blood pressure variability.

OBJECTS OF THE INVENTION

An object of the present invention is to provide an apparatus and a method for obtaining relevant characteristic parameters and indexes of tonoarteriogram signals.

Another object of the present invention is to provide a novel solution to overcome the above problems and/or to provide a useful alternative to the prior art.

One skilled in the art will derive from the following description other objects of the invention. Therefore, the foregoing statements of object are not exhaustive and serve merely to illustrate some of the many objects of the present invention.

SUMMARY OF THE INVENTION

In a first main aspect, the present invention provides an apparatus for obtaining relevant characteristic parameters and indexes of tonoarteriogram (TAG) signals, comprising: a signal acquisition module for acquiring TAG signals from a target subject, a signal processing module for obtaining relevant characteristic parameters and indexes of TAG signals from target subject by calculating and processing through a predetermined mathematical model and a statistical algorithm, wherein the relevant characteristic parameters and indexes of TAG signals include at least one of root mean square value of continuous blood pressure (RMSBP) and standard deviation of continuous blood pressure (SDBP), an evaluation module for evaluating the status of continuous blood pressure of target subject based on characteristic parameters and indexes obtained from the target subject, an alarm module for initiating an alarm when the relevant characteristic parameters and indexes of TAG signals monitored to be abnormal.

Preferably, the signal acquisition module comprises at least: a continuous blood pressure sensor for acquiring TAG signals of target subject.

Preferably, the continuous blood pressure sensor comprises one or more of a multi-wavelength photoplethysmogram (PPG) sensor, a single-wavelength PPG sensor, an electrocardiogram (ECG) sensor, and a pressure sensor.

Preferably, the single PPG sensor of the multi-wavelength PPG sensor, the single-wavelength PPG sensor, the ECG sensor, and the pressure sensor are further used to obtain information on the rhythm and amplitude of the heartbeat.

Preferably, the continuous blood pressure sensor includes a normal mode and a power saving mode.

Preferably, the continuous blood pressure sensor is operated in the normal mode.

Preferably, one or more of the single PPG sensor of the multi-wavelength PPG sensor, the single-wavelength PPG sensor, the ECG sensor, and the pressure sensor are operated in power saving mode for obtaining information on the rhythm and amplitude of the heartbeat.

Preferably, in the power saving mode, if a change in the rhythm and amplitude of the heartbeat of target subject monitored exceeding a predetermined threshold, the power saving mode is automatically turned off and the continuous blood pressure sensor is restarted to acquire the TAG signals of target subject.

Preferably, the signal processing module is further used to process the TAG signals of target subject through a first predetermined formula to obtain RMSBP of target subject; wherein the first predetermined formula is based on statistically calculation in the normal mode, $$RMSBP = rmsv[\text{tag}(t)] = \sqrt{\frac{1}{N}\sum_{i=1}^{N}x_i^2}$$

where $x_i$ is the continuous blood pressure value, N is the number of data points, rmsv is the root mean square value, and tag is the continuous blood pressure signal; wherein the first predetermined formula is based on estimation from a mathematical model in power saving mode, $$RMSBP = \sqrt{\overline{a}^2 \lambda h + d^2}$$

where $\overline{a}$ is the average pulse pressure within predetermined monitoring period, $\lambda$ is the average heart rate within predetermined monitoring period $\lambda = E[1/(T_{i+1} - T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \; h_{tag}(t)$$

is a continuous blood pressure waveform with a mean amplitude of 0 within one cardiac cycle, t indicates time, d is a predetermined constant represents for DC component of the blood pressure waveform, and E indicates the mean value.

Preferably, the signal processing module is further used to process the TAG signals of target subject to obtain SDBP through a second predetermined formula; wherein the second predetermined formula is based on statistically calculation in the normal mode, $$SDBP = std[tag(t)] = \sqrt{\frac{1}{N-1} \sum_{i=1}^{N} |x_i - \mu|^2}$$

where $x_i$ is the continuous blood pressure value, N is the number of data points, $\mu$ is the mean of continuous blood pressure value, and std is the standard deviation. tag is the continuous blood pressure signal; wherein the second predetermined formula is based on estimation from a mathematical model in power saving mode, $$SDBP = \overline{a}\sqrt{\lambda h}$$

where $\overline{a}$ is the average pulse pressure within predetermined monitoring period, $\lambda$ is the average heart rate within predetermined monitoring period $\lambda = E[1/(T_{i+1} - T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \; h_{tag}(t)$$

is a continuous blood pressure waveform with a mean amplitude of 0 within one cardiac cycle, t indicates time and E indicates the mean value.

Preferably, the evaluation module is further used to generate continuous blood pressure level assessment based on the RMSBP, the continuous blood pressure level assessment is used to characterize the overall blood pressure level of the target subject.

Preferably, the evaluation module is used to generate continuous blood pressure variability assessment based on the SDBP, the continuous blood pressure variability assessment is used to characterize the continuous blood pressure variability of the target subject.

Preferably, the relevant characteristic parameters and indexes of TAG signals are further used to characterize any one of heart rate, pulse pressure, blood pressure waveform and vascular compliance of the target subject.

Preferably, the relevant characteristic parameters and indexes of TAG signals are further used for classification of target subject, the classification of target subject includes a hypertensive category.

Preferably, the alarm module has the forms of one or more of local alarm to call for help, sending an alarm message to an emergency contact of target user and sending an alarm message to emergency center.

Preferably, the apparatus is implemented in a wearable, unobtrusive continuous blood pressure measuring device, the forms of the device include one or more of a cell phone, a watch, a bracelet, a ring, a wristband, and a vest.

In a second main aspect, the present invention provides a method for obtaining relevant characteristic parameters and indexes of TAG signals, comprising: acquiring TAG signals from a target subject, obtaining relevant characteristic parameters and indexes of TAG signals from target subject by calculating and processing through a predetermined mathematical model and a statistical algorithm, wherein the relevant characteristic parameters and indexes of TAG signals include at least one of RMSBP and SDBP, evaluating the status of continuous blood pressure of target subject based on characteristic parameters and indexes obtained from the target subject, initiating an alarm when the relevant characteristic parameters and indexes of TAG signals monitored to be abnormal.

Preferably, the method includes a normal mode and a power saving mode.

Preferably, in the normal mode, the TAG signals of target subject are acquired.

Preferably, in the power saving mode, the information on the rhythm and amplitude of the heartbeat of target subject is obtained.

Preferably, in the power saving mode, if a change in the rhythm and amplitude of the heartbeat of target subject monitored exceeding a predetermined threshold, the power saving mode is automatically turned off and the continuous blood pressure sensor is restarted to acquire the TAG signals of target subject.

Preferably, the obtaining relevant characteristic parameters and indexes of TAG signals from target subject by calculating and processing through a predetermined mathematical model and a statistical algorithm, comprises processing the TAG signals of target subject through a first predetermined formula to obtain RMSBP of target subject; wherein the first predetermined formula is based on statistically calculation in the normal mode, $$RMSBP = rmsv[tag(t)] = \sqrt{\frac{1}{N} \sum_{i=1}^{N} x_i^2}$$

where $x_i$ is the continuous blood pressure value, N is the number of data points, rmsv is the root mean square value, and tag is the continuous blood pressure signal; wherein the first predetermined formula is based on estimation from a mathematical model in power saving mode, $$RMSBP = \sqrt{\bar{a}^2 \lambda h + d^2}$$

where $\bar{a}$ is the average pulse pressure within predetermined monitoring period, $\lambda$ is the average heart rate within predetermined monitoring period $\lambda = E[1/(T_{i+1} - T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \ h_{tag}(t)$$

is a continuous blood pressure waveform with a mean amplitude of 0 within one cardiac cycle, t indicates time, d is a predetermined constant represents for DC component of the blood pressure waveform, and E indicates the mean value.

Preferably, the obtaining relevant characteristic parameters and indexes of TAG signals from target subject by calculating and processing through a predetermined mathematical model and a statistical algorithm, further comprises:

processing the TAG signals of target subject to obtain SDBP through a second predetermined formula; wherein the second predetermined formula is based on statistically calculation in the normal mode, $$SDBP = std[\text{tag}(t)] = \sqrt{\frac{1}{N-1}\sum_{i=1}^{N}|x_i - \mu|^2}$$

where $x_i$ is the continuous blood pressure value, N is the number of data points, $\mu$ is the mean of continuous blood pressure value, and std is the standard deviation. tag is the continuous blood pressure signal; wherein the second predetermined formula is based on estimation from a mathematical model in power saving mode, $$SDBP = \bar{a}\sqrt{\lambda h}$$

where $\bar{a}$ is the average pulse pressure within predetermined monitoring period, $\lambda$ is the average heart rate within predetermined monitoring period $\lambda = E[1/(T_{i+1} - T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \ h_{tag}(t)$$

is a continuous blood pressure waveform with a mean amplitude of 0 within one cardiac cycle, t indicates time and E indicates the mean value.

Preferably, the evaluating the status of continuous blood pressure of target subject based on characteristic parameters and indexes obtained from the target subject, comprises:

generating continuous blood pressure level assessment based on the RMSBP, the continuous blood pressure level assessment is used to characterize the overall blood pressure level of the target subject.

Preferably, the evaluating the status of continuous blood pressure of target subject based on characteristic parameters and indexes obtained from the target subject, further comprises:

generating continuous blood pressure variability assessment based on the SDBP, the continuous blood pressure variability assessment is used to characterize the continuous blood pressure variability of the target subject.

Preferably, the initiating an alarm includes one or more forms of local alarm to call for help, sending an alarm message to an emergency contact of the target user, and sending an alarm message to emergency center.

Preferably, the method is implemented in a wearable, unobtrusive continuous blood pressure measurement device, the forms of the device include one or more of a cell phone, a watch, a bracelet, a ring, a wristband, and a vest.

In a third main aspect, the present invention provides an electronic device comprising a memory, a processor, and a computer program stored in the memory and runnable on the processor, the processor executing the program to implement the steps of the method as provided in the second aspect.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figures, of which:

FIG. 2a is a trend of root mean square value of continuous blood pressure (RMSBP) calculated statistically in normal mode according to an embodiment of the present invention;

FIG. 2b is a trend of RMSBP estimated from a mathematical model in power saving mode according to an embodiment of the present invention;

FIG. 2c is a trend of the percentage error of the RMSBP derived from two different modes according to an embodiment of the present invention;

FIG. 2d is a scatter plot of the statistically calculated RMSBP versus mean systolic blood pressure in normal mode according to an embodiment of the present invention;

FIG. 3a is a trend of the standard deviation of beat-to-beat diastolic blood pressure according to an embodiment of the present invention;

FIG. 3b is a trend of the standard deviation of beat-to-beat systolic blood pressure according to an embodiment of the present invention;

7

8

Figures 4A, 4B, 4C, 4D:
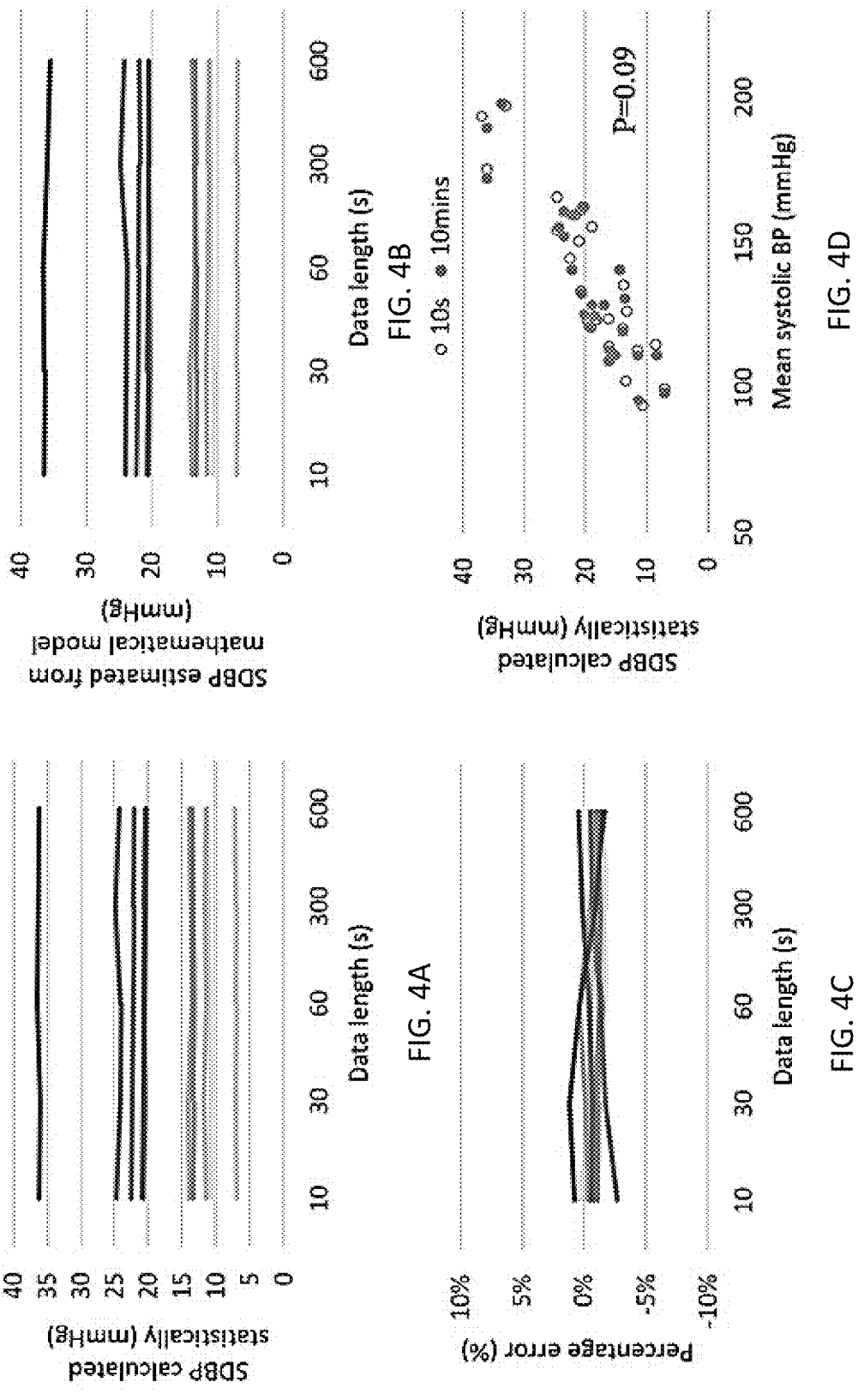
Figure 5:
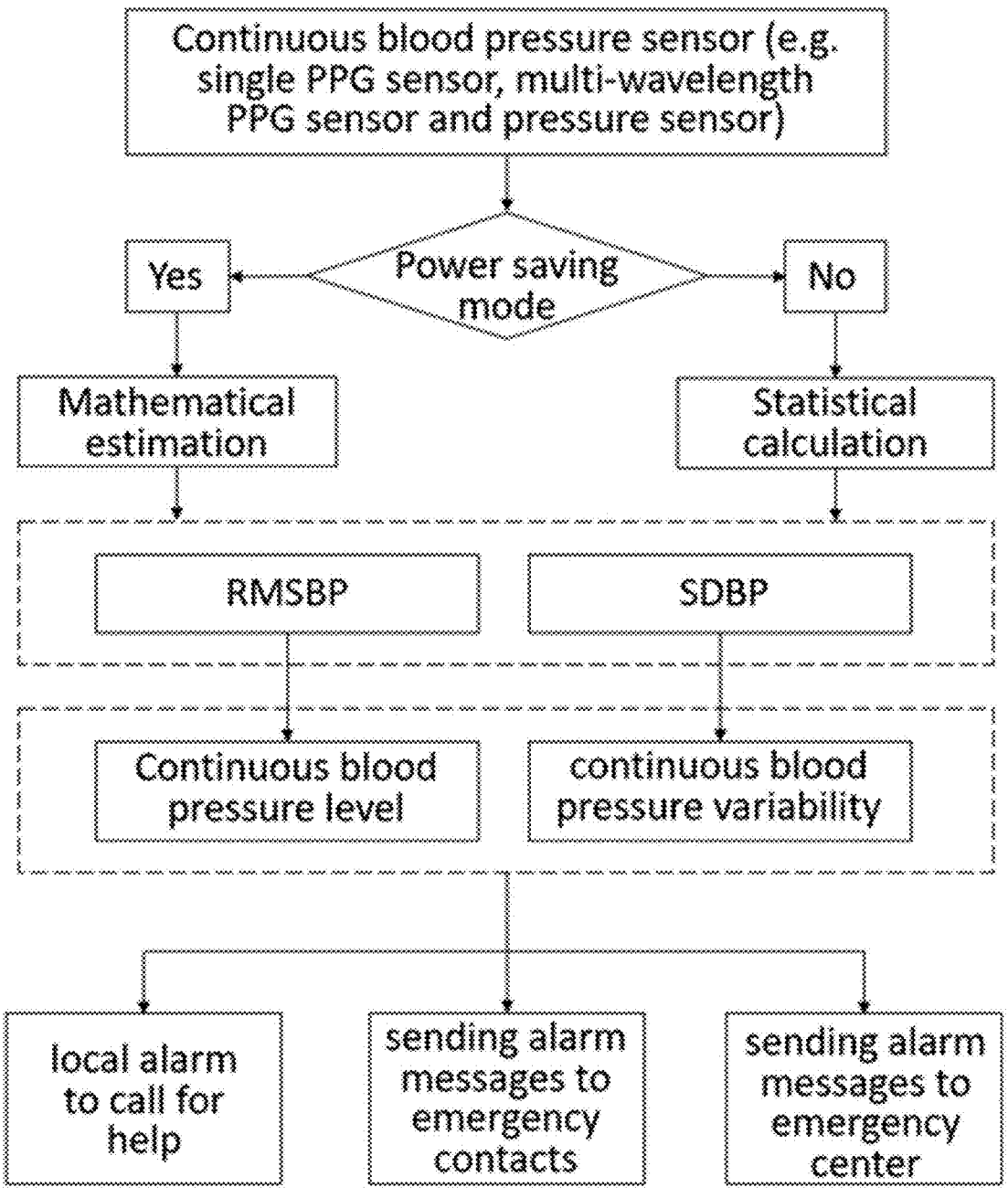
Figure 6:
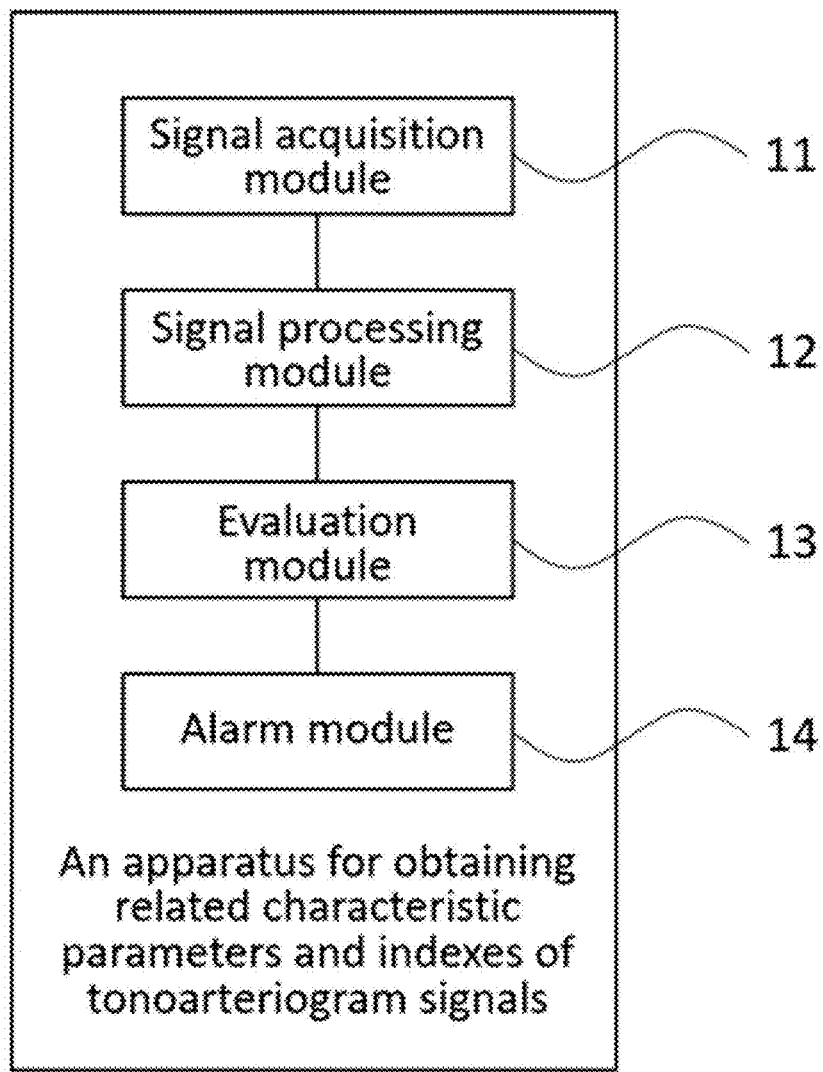
Figure 7:
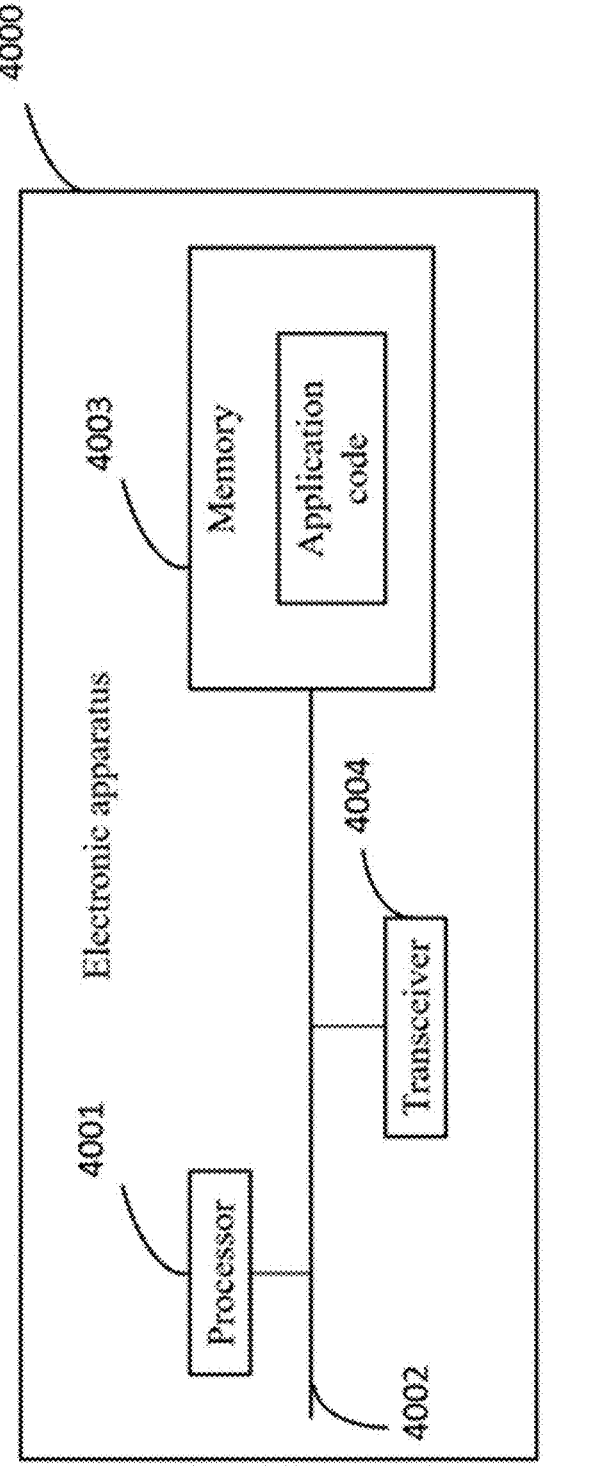

FIG. 3*c* is a scatter plot of the standard deviation of beat-to-beat diastolic blood pressure versus the mean systolic blood pressure according to an embodiment of the present invention;

FIG. 3*d* is a scatter plot of a standard deviation of beat-to-beat systolic blood pressure versus mean systolic blood pressure according to an embodiment of the present invention;

FIG. 4*a* is a trend of standard deviation of continuous blood pressure (SDBP) calculated statistically in normal mode according to an embodiment of the present invention;

FIG. 4*b* is a trend of SDBP estimated from a mathematical model in power saving mode according to an embodiment of the present invention;

FIG. 4*c* is a trend of the percentage error of the SDBP derived from two different modes according to an embodiment of the present invention;

FIG. 4*d* is a scatter plot of the statistically calculated SDBP versus mean systolic blood pressure in normal mode according to an embodiment of the present invention;

FIG. 5 is a flowchart illustrating a processing method for obtaining relevant characteristic parameters and indexes of TAG signals according to an embodiment of the present invention;

FIG. 6 is a schematic diagram of the structure of an apparatus for obtaining relevant characteristic parameters and indexes of TAG signals according to an embodiment of the present invention; and FIG. 7 is a schematic diagram of a structure of an electronic device according to an embodiment of the present invention.

DESCRIPTION OF PREFERRED EMBODIMENTS

Hereinafter, an embodiment of the present invention will be described in detail with reference to the drawings, wherein the same or similar designations from beginning to end indicate the same or similar components or components having the same or similar functions. The embodiment described below by reference to the accompanying drawings are exemplary and are intended only to explain the present application and are not to be construed as limiting the present invention.

It will be understood by those of skill in the art that the singular forms "one", "a" and "the" as used herein may also include the plural forms, unless otherwise stated. It should be further understood that the wording "includes" as used in the specification of this application refers to the presence of features, integers, steps, operations, components and/or assemblies, but does not preclude the presence or addition of one or more other features, integers, steps, operations, components, assemblies and/or groups thereof. It should be understood that when an embodiment of this application refers to a component being "connected" or "coupled" to another component, it may be directly connected or coupled to other components, or there may be intermediate components. In addition, "connected" or "coupled" as used herein may include wirelessly connected or wirelessly coupled. The word "and/or" as used herein includes all or any of the units and all combinations of one or more of the associated listed items.

In order to make the purpose, technical solutions and advantages of this application clearer, the following will be described in further detail in conjunction with the accompanying drawings for the implementation of this application.

The present invention provides a method and an apparatus for obtaining relevant characteristic parameters and indexes of tonoarteriogram (TAG) signals. A signal acquisition module acquires TAG signals from a target subject; a signal processing module obtains relevant characteristic parameters and indexes of continuous blood pressure from obtained TAG signals of target subject by calculating and processing through a predetermined mathematical model and a statistical algorithm, wherein the relevant characteristic parameters and indexes of continuous blood pressure include at least one of root mean square value of continuous blood pressure (RMSBP) and standard deviation of continuous blood pressure (SDBP), an evaluation module evaluates the status of continuous blood pressure based on characteristic parameters and indexes obtained from the target subject, an alarm module initiates an alarm when the relevant characteristic parameters and indexes of continuous blood pressure monitored to be abnormal, which allows to monitor the blood pressure of the target user at different period of time, realizing rapid blood pressure measurement, and enabling timely alarms to ensure the safety of the target user.

Definitions of Terms

1) Diastolic Pressure

When the human heart is diastolic, the pressure generated by the elastic retraction of the arterial blood vessels is called diastolic pressure, also called low pressure. When the heart is diastolic, the aortic pressure drops, the lowest arterial blood pressure at the end of diastole called diastolic pressure.

2) Systolic Pressure

When the human heart contracts, the pressure in the arteries rises, and in the middle of the heart contraction, the pressure in the arteries is the highest, at which time the pressure of blood on the inner wall of the blood vessels is called systolic pressure, also known as high pressure.

(3) Blood Pressure

Blood pressure (BP) refers to the pressure per unit area applied on the vessel wall when blood flows in the blood vessels. It is called arterial blood pressure, capillary pressure and venous blood pressure respectively in different blood vessels, and the blood pressure usually referred to is the arterial blood pressure of body circulation.

(4) Mean Blood Pressure

Mean arterial pressure (MAP) refers to the average value of arterial blood pressure during a cardiac cycle.

5) Blood Pressure Variability

The degree of blood pressure fluctuation within a certain period of time is blood pressure variability. Usually, we use the standard deviation of ambulatory blood pressure (SD, standard deviation) and the coefficient of variability (CV, coefficient of variability, the ratio of the standard deviation of ambulatory blood pressure to the mean SD/mean) to express the blood pressure variability or the degree of overall change in blood pressure over a period of time.

6) Pulse Pressure

Pulse pressure refers to the difference between systolic and diastolic blood pressure. Pulse pressure reflects the magnitude of the fluctuation during a cardiac cycle.

7) Blood Pressure Level

Blood pressure level refers to a medical classification and definition of the human blood pressure condition, which currently includes: normotension, prehypertension, stage 1 hypertension, stage 2 hypertension.

For wearable and mobile health applications, there is a strong need for reliable ultra-short-term metric of continuous blood pressure to avoid motion artifacts and to meet the need for rapid diagnosis of acute cardiovascular disease. While both mid- and long-term methods of analyzing blood pressure variability have been extensively studied in data from normal and cardiac patients, there is a lack of research on more effective methods for assessing ultra-short-term and short-term blood pressure levels and blood pressure variability.

The present embodiment provides a method and apparatus for obtaining relevant characteristic parameters and indexes of tonoarteriogram (TAG) signals, aiming to solve not only the technical problems of the prior art as described above, but also, and more importantly, the technical problem of relevant parameters extraction and evaluation from a novel, unobtrusive continuous blood pressure, also called TAG signal, which consists of continuous blood pressure waveforms within each cardiac cycle. The present application can be applied in, for example, wearable devices, computers, cell phones, medical measurement devices (e.g., a sphygmomanometer, etc.), chips, and other electronic devices, and the present application embodiments are not specifically limited.

Figure 1:
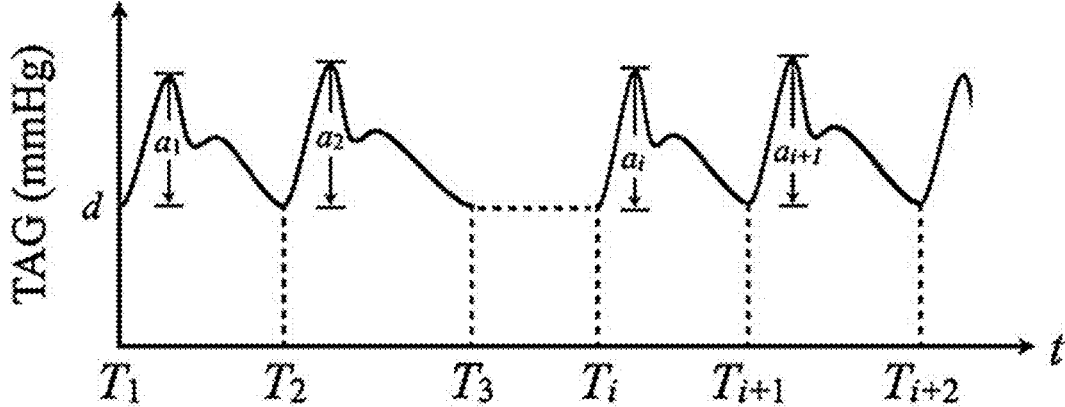
FIG. 1 is a schematic diagram of a tonoarteriogram (TAG) signal according to an embodiment of the present invention.

In an embodiment, FIG. 1 is a schematic diagram of a TAG signal according to an embodiment of the present invention. As shown in FIG. 1, the TAG signal comprises a continuous blood pressure waveform within each cardiac cycle, which may be represented as:

$$\mathrm{tag}(t) = p(t) * [a_i \cdot h_{tag}(t)] + d(t)$$

where $a_i$ is the pulse pressure per beat, $h_{tag}(t)$ is a continuous blood pressure waveform with a mean amplitude of 0 within one cardiac cycle, and $d(t)$ is the DC component of the blood pressure waveform. $p(t)$ is a sequence of beat pulses, which can be expressed as:

$$p(t) = \sum_{i=-\infty}^{\infty} \delta(t - T_i)$$

where $T_i$ is a random variable representing the onset time of each beat blood pressure and $\delta$ denotes the impulse function.

According to the mathematical model given above, the mean value of the TAG signal, with blood pressure variability and heart rate variability independent of each other, is $$E[\mathrm{tag}(t)] = E[a_i] \int_{-\infty}^{\infty} h_{tag}(t) E\left\{ \sum_{i=-\infty}^{\infty} \delta(\tau - t - T_i) \right\} dt + d(t) =$$

$$\bar{a}\lambda \int_{-\infty}^{\infty} h_{tag}(t) dt + \bar{d} = \bar{a}\lambda \overline{h_{tag}(t)} + \bar{d}$$

where $\bar{a}$ is the mean pulse pressure, $\overline{h_{tag}(t)}$ is the mean amplitude of the continuous blood pressure waveform within each cardiac cycle, $E$ denotes the mean value, and $\lambda$ is the mean heart rate, $\lambda = E[1/(T_{i+1} - T_i)]$.

In addition, in the case where each continuous blood pressure waveform $h_{tag}(t)$ does not overlap each other and the mean value is 0 within each cardiac cycle, $d(t)$ is set as a constant, $$\overline{h_{tag}(t)} = \int_{-\infty}^{\infty} h_{tag}(t) dt = 0, \bar{d} = E[d(t)] = d$$

10 thus, it is obtained that $$E[\mathrm{tag}(t)] = \bar{d} = d$$

then the mean square value of the TAG signal is $$E[\mathrm{tag}^2(t)] = \bar{a}^2 \cdot E\{[p(t) * h_{tag}(t) + d(t)]^2\} =$$

$$\bar{a}^2 \cdot E\{[p(t) * h_{tag}(t)]^2 + d^2(t) + 2p(t) * h_{tag}(t) \cdot d(t)\}$$

$$\text{For } \overline{h_{tag}(t)} = \int_{-\infty}^{\infty} h_{tag}(t) dt = 0, d(t) = d,$$

$$E[\mathrm{tag}^2(t)] = \bar{a}^2 \cdot E\{[p(t) * h_{tag}(t)]^2 + d^2 + 2d \cdot p(t) * h_{tag}(t)\} =$$

$$\bar{a}^2 \int_{-\infty}^{\infty} h_{tag}^2(t) E\left\{ \sum_{i=-\infty}^{\infty} \delta(\tau - t - T_i) \right\} dt + d^2$$

thus, it is obtained that $$E[\mathrm{tag}^2(t)] = \bar{a}^2 \lambda \int_{-\infty}^{\infty} h_{tag}^2(t) dt + d^2 = \bar{a}^2 \lambda h + d^2 \text{ where}$$

$$h = \int_{-\infty}^{\infty} h_{tag}^2(t) dt.$$

Accordingly, the variance can be derived as:

$$\mathrm{var}[\mathrm{tag}(t)] = E[\mathrm{tag}^2(t)] - E[\mathrm{tag}(t)]^2 = \bar{a}^2 \lambda h + d^2 - d^2 = \bar{a}^2 \lambda h$$

Further, $$std[\mathrm{tag}(t)] = \bar{a}\sqrt{\lambda h}$$

A new metrics that can be used to assess continuous blood pressure levels and variability, including the root mean square value of continuous blood pressure (RMSBP); and the standard deviation of continuous blood pressure (SDBP).

One mathematical model of the RMSBP is RMSBP= $\sqrt{\bar{a}^2 \lambda h + d^2}$, and one mathematical model of the SDBP is SDBP= $\bar{a}\sqrt{\lambda h}$.

Based on the theory, it can be seen that the RMSBP and the SDBP reflect information about human heart rate, pulse pressure, blood pressure waveform, and peripheral vascular compliance.

FIGS. 2a, 2b, and 2c show the trend of RMSBP for 10 subjects in normal mode and in power saving mode, respectively, with different data lengths, and the trend of the percentage error of the RMSBP derived from two different modes, while FIG. 2d shows the scatter plot of the statistically calculated RMSBP versus mean systolic blood pressure for 26 subjects in normal mode. As shown in FIG. 2, the percentage error of the RMSBP derived from two different modes were within 5%, and RMSBP values were stable over different data lengths, with no statistically significant difference between the statistically calculated RMSBP values over 10 seconds and 10 minutes (p=0.54). The ultra-short-term RMSBP measurements can be used for the assessment of blood pressure levels.

FIGS. 3a and 3b show the trend of the standard deviation of beat-to-beat diastolic/systolic blood pressure for 10 subjects with different data lengths, respectively, and FIG. 3c is scatter plot of the standard deviation of beat-to-beat diastolic blood pressure versus the mean systolic blood pressure for 26 subjects. As shown in FIG. 3, beat-to-beat diastolic/systolic blood pressure standard deviation fluctuated widely over different lengths, and there was a statistically significant difference between the beat-to-beat diastolic/systolic standard deviation over 10 seconds and 10 minutes (p=0.0012, p<0.0001).

FIGS. 4a, 4b, and 4c show the trend of SDBP for 10 subjects in the normal mode and in the power saving mode, respectively, with different data lengths, and the trend of the percentage error of the SDBP derived from two different modes, while FIG. 4d shows the scatter plot of the statistically calculated SDBP versus mean systolic blood pressure for 26 subjects in normal mode. As shown in FIG. 4, the percentage error of the SDBP derived from two different modes were within 3%, and SDBP values were more stable over different data lengths compared with traditional blood pressure variability index:standard deviation of beat-to-beat diastolic/systolic blood pressure measured over a specific period of time, and no statistically significant difference between the statistically calculated SDBP over 10 seconds and 10 minutes (p=0.09). The ultra-short-term SDBP measurements could be used to assess blood pressure variability.

The present invention further provides a method for obtaining relevant characteristic parameters and indexes of TAG signals, comprising: acquiring TAG signals from a target subject, obtaining relevant characteristic parameters and indexes of TAG signals from target subject by calculating and processing through a predetermined mathematical model and a statistical algorithm, wherein the relevant characteristic parameters and indexes of TAG signals include at least one of RMSBP and SDBP, evaluating the status of continuous blood pressure of target subject based on characteristic parameters and indexes obtained from the target subject, initiating an alarm when the relevant characteristic parameters and indexes of TAG signals monitored to be abnormal.

In an embodiment, the method includes a normal mode and a power saving mode.

In an embodiment, in the normal mode, the TAG signals of target subject are acquired.

In an embodiment, in the power saving mode, the information on the rhythm and amplitude of the heartbeat of target subject is obtained.

In an embodiment, in the power saving mode, if a change in the rhythm and amplitude of the heartbeat of target subject monitored exceeding a predetermined threshold, the power saving mode is automatically turned off and the continuous blood pressure sensor is restarted to acquire the TAG signals of target subject.

In an embodiment, the obtaining relevant characteristic parameters and indexes of TAG signals from target subject by calculating and processing through a predetermined mathematical model and a statistical algorithm, comprises: processing the TAG signals of target subject through a first predetermined formula to obtain RMSBP of target subject. The first predetermined formula is based on statistically calculation in the normal mode, $$RMSBP = rmsv[tag(t)] = \sqrt{\frac{1}{N}\sum_{i=1}^{N} x_i^2}$$

where $x_i$ is the continuous blood pressure value, N is the number of data points, rmsv is the root mean square value, and tag is the continuous blood pressure signal. The first predetermined formula is based on estimation from a mathematical model in power saving mode, $$RMSBP = \sqrt{\bar{a}^2 \lambda h + d^2}$$

where $\bar{a}$ is the average pulse pressure within predetermined monitoring period, $\lambda$ is the average heart rate within predetermined monitoring period $\lambda=E[1/(T_{i+1}-T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \ h_{tag}(t)$$

is a continuous blood pressure waveform with a mean amplitude of 0 within one cardiac cycle, t indicates time, d is a predetermined constant represents for DC component of the blood pressure waveform, and E indicates the mean value.

In an embodiment, the obtaining relevant characteristic parameters and indexes of TAG signals from target subject by calculating and processing through a predetermined mathematical model and a statistical algorithm, further comprises:

processing the TAG signals of target subject to obtain SDBP through a second predetermined formula. The second predetermined formula is based on statistically calculation in the normal mode, $$SDBP = std[tag(t)] = \sqrt{\frac{1}{N-1}\sum_{i=1}^{N} |x_i - \mu|^2}$$

where $x_i$ is the continuous blood pressure value, N is the number of data points, $\mu$ is the mean of continuous blood pressure value, and std is the standard deviation. tag is the continuous blood pressure signal. The second predetermined formula is based on estimation from a mathematical model in power saving mode, $$SDBP = \bar{a}\sqrt{\lambda h}$$

where $\bar{a}$ is the average pulse pressure within predetermined monitoring period, $\lambda$ is the average heart rate within predetermined monitoring period $\lambda=E[1/(T_{i+1}-T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \ h_{tag}(t)$$

is a continuous blood pressure waveform with a mean amplitude of 0 within one cardiac cycle, t indicates time and E indicates the mean value.

In an embodiment, the evaluating the status of continuous blood pressure of target subject based on characteristic parameters and indexes obtained from the target subject, comprises: generating continuous blood pressure level assessment based on the RMSBP, the continuous blood pressure level assessment is used to characterize the overall blood pressure level of the target subject.

In an embodiment, the evaluating the status of continuous blood pressure of target subject based on characteristic parameters and indexes obtained from the target subject, further comprises: generating continuous blood pressure variability assessment based on the SDBP, the continuous blood pressure variability assessment is used to characterize the continuous blood pressure variability of the target subject.

In an embodiment, the initiating an alarm includes one or more forms of local alarm to call for help, sending an alarm message to an emergency contact of the target user, and sending an alarm message to emergency center.

In an embodiment, the method is implemented in a wearable, unobtrusive continuous blood pressure measurement device, the forms of the device include one or more of a cell phone, a watch, a bracelet, a ring, a wristband, and a vest.

The method for obtaining relevant characteristic parameters and indexes of TAG signals provided by the embodiment of the present invention is described in detail in the above embodiment of the apparatus for obtaining relevant characteristic parameters and indexes of TAG signals and will not be described herein.

FIG. 6 is a schematic diagram of the structure of an apparatus for obtaining relevant characteristic parameters and indexes of TAG signals provided by an embodiment of the present invention.

The present invention provides a method and an apparatus for obtaining relevant characteristic parameters and indexes of TAG signals. A signal acquisition module acquires TAG signals from a target subject; a signal processing module obtains relevant characteristic parameters and indexes of continuous blood pressure from obtained TAG signals of target subject by calculating and processing through a predetermined mathematical model and a statistical algorithm, wherein the relevant characteristic parameters and indexes of continuous blood pressure include at least one of RMSBP and SDBP, an evaluation module evaluates the status of continuous blood pressure based on characteristic parameters and indexes obtained from the target subject, an alarm module initiates an alarm when the relevant characteristic parameters and indexes of continuous blood pressure monitored to be abnormal, which allows to monitor the blood pressure of the target user at different period of time, realizing rapid blood pressure measurement, and enabling timely alarms to ensure the safety of the target user.

The present invention provides an apparatus for obtaining relevant characteristic parameters and indexes of TAG signals, as shown in FIG. 6, comprising a signal acquisition module 11, a signal processing module 12, an evaluation module 13, and an alarm module 14, specifically, a signal acquisition module 11 for acquiring TAG signals from a target subject, a signal processing module 12 for obtaining relevant characteristic parameters and indexes of TAG signals from target subject by calculating and processing through a predetermined mathematical model and a statistical algorithm, wherein the relevant characteristic parameters and indexes of TAG signals include at least one of RMSBP and SDBP, an evaluation module 13 for evaluating the status of continuous blood pressure of target subject based on characteristic parameters and indexes obtained from the target subject, an alarm module 14 for initiating an alarm when the relevant characteristic parameters and indexes of TAG signals monitored to be abnormal.

In an embodiment, the signal acquisition module 11 comprises at least: a continuous blood pressure sensor for acquiring TAG signals of target subject.

In an embodiment, the continuous blood pressure sensor comprises one or more of a multi-wavelength photoplethysmogram (PPG) sensor, a single-wavelength PPG sensor, an electrocardiogram (ECG) sensor, and a pressure sensor.

In an embodiment, the single PPG sensor of the multi-wavelength PPG sensor, the single-wavelength PPG sensor, the ECG sensor, and the pressure sensor are further used to obtain information on the rhythm and amplitude of the heartbeat.

In an embodiment, the continuous blood pressure sensor includes a normal mode and a power saving mode.

In an embodiment, the continuous blood pressure sensor is operated in the normal mode.

In an embodiment, one or more of the single PPG sensor of the multi-wavelength PPG sensor, the single-wavelength PPG sensor, the ECG sensor, and the pressure sensor are operated in power saving mode for obtaining information on the rhythm and amplitude of the heartbeat.

In an embodiment, in the power saving mode, if a change in the rhythm and amplitude of the heartbeat of target subject monitored exceeding a predetermined threshold, the power saving mode is automatically turned off and the continuous blood pressure sensor is restarted to acquire the TAG signals of target subject.

In an embodiment, the signal processing module 12 is further used to process the TAG signals of target subject through a first predetermined formula to obtain RMSBP of target subject. The first predetermined formula is based on statistically calculation in the normal mode, $$RMSBP = rmsv[tag(t)] = \sqrt{\frac{1}{N}\sum_{i=1}^{N} x_i^2}$$

where $x_i$ is the continuous blood pressure value, N is the number of data points, rmsv is the root mean square value, and tag is the continuous blood pressure signal. The first predetermined formula is based on estimation from a mathematical model in power saving mode, $$RMSBP = \sqrt{\bar{a}^2 \lambda h + d^2}$$

where $\bar{a}$ is the average pulse pressure within predetermined monitoring period, $\lambda$ is the average heart rate within predetermined monitoring period $\lambda = E[1/(T_{i+1}-T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \; h_{tag}(t)$$

is a continuous blood pressure waveform with a mean amplitude of 0 within one cardiac cycle, t indicates time, d is a predetermined constant represents for DC component of the blood pressure waveform, and E indicates the mean value.

In an embodiment, the signal processing module 12 is further used to process the TAG signals of target subject to obtain SDBP through a second predetermined formula. The second predetermined formula is based on statistically calculation in the normal mode, $$SDBP = std[tag(t)] = \sqrt{\frac{1}{N-1}\sum_{i=1}^{N}|x_i - \mu|^2}$$

where $x_i$ is the continuous blood pressure value, N is the number of data points, $\mu$ is the mean of continuous blood pressure value, and std is the standard deviation. tag is the continuous blood pressure signal. The second predetermined formula is based on estimation from a mathematical model in power saving mode, $$SDBP = \bar{a}\sqrt{\lambda h}$$

where $\bar{a}$ is the average pulse pressure within predetermined monitoring period, $\lambda$ is the average heart rate within predetermined monitoring period $\lambda = E[1/(T_{i+1}-T_i)]$, $T_i$, $T_{i+1}$ are random variables to indicate the onset of blood pressure waveform per beat within predetermined monitoring period, h is the average strength of the blood pressure waveform within predetermined monitoring period $$h = \int_{-\infty}^{\infty} h_{tag}^2(t)dt, \ h_{tag}(t)$$

is a continuous blood pressure waveform with a mean amplitude of 0 within one cardiac cycle, t indicates time and E indicates the mean value.

In an embodiment, the evaluation module 13 is further used to generate continuous blood pressure level assessment based on the RMSBP, the continuous blood pressure level assessment is used to characterize the overall blood pressure level of the target subject.

In an embodiment, the evaluation module 13 is used to generate continuous blood pressure variability assessment based on the SDBP, the continuous blood pressure variability assessment is used to characterize the continuous blood pressure variability of the target subject.

In an embodiment, the relevant characteristic parameters and indexes of TAG signals are further used to characterize any one of heart rate, pulse pressure, blood pressure waveform and vascular compliance of the target subject.

In an embodiment, the relevant characteristic parameters and indexes of TAG signals are further used for classification of target subject, the classification of target subject includes a hypertensive category.

In an embodiment, the alarm module 14 has the forms of one or more of local alarm to call for help, sending an alarm message to an emergency contact of target user and sending an alarm message to emergency center.

In an embodiment, the apparatus is implemented in a wearable, unobtrusive continuous blood pressure measurement device, the forms of the device include one or more of a cell phone, a watch, a bracelet, a ring, a wristband, and a vest.

The present invention provides an electronic device comprising a memory, a processor, and at least one program, stored in the memory, for execution by the processor to realize, when compared to the prior art: a signal acquisition module acquires TAG signals from a target subject; a signal processing module obtains relevant characteristic parameters and indexes of continuous blood pressure from obtained TAG signals of target subject by calculating and processing through a predetermined mathematical model and a statistical algorithm, wherein the relevant characteristic parameters and indexes of continuous blood pressure include at least one of RMSBP and SDBP, an evaluation module evaluates the status of continuous blood pressure based on characteristic parameters and indexes obtained from the target subject, an alarm module initiates an alarm when the relevant characteristic parameters and indexes of continuous blood pressure monitored to be abnormal, which allows to monitor the blood pressure of the target user at different period of time, realizing rapid blood pressure measurement, and enabling timely alarms to ensure the safety of the target user.

In an optional embodiment, there is provided an electronic device, as shown in FIG. 7, the electronic device 4000 comprises: a processor 4001 and a memory 4003, wherein the processor 4001 and the memory 4003 are connected, e.g., via a bus 4002. Optionally, the electronic device 4000 may also include a transceiver 4004. It is noted that the transceiver 4004 is not limited to one in practical applications, and the structure of the electronic device 4000 does not constitute a limitation of an embodiment of this application.

The processor 4001 may be a CPU (Central Processing Unit), a general-purpose processor, a DSP (Digital Signal Processor), an ASIC (Application Specific Integrated Circuit), an FPGA (FPGA), or a FPC (Fibre Optic Integrated Circuit). Integrated Circuit), FPGA (Field Programmable Gate Array) or other programmable logic device, transistorized logic device, hardware component, or any combination thereof. It may implement or execute various exemplary logic boxes, modules, and circuits described in conjunction with the disclosure of this application. Processor 4001 may also be a combination that implements computing function, such as a combination containing one or more microprocessors, a combination of a DSP and a microprocessor, etc.

The bus 4002 may include a pathway to transfer information between above components. Bus 4002 may be a PCI (Peripheral Component Interconnect) bus or an EISA (Extended Industry Standard Architecture) bus, for example. Bus 4002 can be divided into address bus, data bus, control bus, etc. For the convenience of representation, only one thick line is used in FIG. 7, but it does not mean that there is only one bus or one type of bus. Memory 4003 can be ROM (Read Only Memory) or other types of static storage devices that can store static information and instructions, RAM (Random Access Memory) or other types of dynamic storage devices that can store information and instructions, or EEPROM (EEPROM (Electrically Erasable Programmable Read Only Memory), CD-ROM (Compact Disc Read Only Memory) or other optical disc storage, optical disc storage (including compressed disc, laser disc, optical disc, digital universal CD-ROM (Compact Disc Read Only Memory, read-only CD-ROM) or other optical disc storage, optical disc storage (including compact disc, laser disc, optical disk, digital universal disc, Blu-ray disc, etc.), disk storage media or other magnetic storage devices, or any other media capable of carrying or storing desired program code in the form of instructions or data structures and capable of being accessed by a computer, but not limited thereof.

Memory 4003 is used to store the application program code for executing the present application solution and is controlled for execution by processor 4001. Processor 4001 is used to execute the application program code stored in memory 4003 to implement what is shown in the foregoing method embodiment.

It should be understood that although the individual steps in the flowchart of the accompanying drawings are shown sequentially as indicated by the arrows, the steps are not necessarily executed sequentially in the order indicated by the arrows. Except as expressly stated herein, there is no strict sequential limitation on the execution of these steps, which may be performed in any other order. Moreover, at least some of the steps in the flowchart of the accompanying drawings may include a plurality of sub-steps or a plurality of phases, which are not necessarily executed at the same moment of completion, but may be executed at different moments, and the order of their execution is not necessarily sequential, but may be executed in rotation or alternately with other steps or at least some of the sub-steps or phases of other steps.

The above is only a partial implementation of the present invention, and it should be noted that for a person of ordinary skill in the art, several improvements and embellishments can be made without departing from the principles of the present invention, and these improvements and embellishments should also be considered as the scope of protection of the present invention.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. An apparatus for detecting abnormality in blood pressure of a target subject for diagnosis of acute cardiovascular disease, the apparatus comprises:

a signal acquisition module comprises at least a continuous blood pressure sensor adapted to operate in a normal mode and a power saving mode, wherein the signal acquisition module detects tonoarteriogram (TAG) signals from a target subject in the normal mode, and detects information on rhythm and amplitude of heartbeat of the target subject in the power saving mode;

wherein, when a change in the rhythm and amplitude of the heartbeat of the target subject is detected to exceed a predetermined threshold when operated in the power saving mode, the signal acquisition module is adapted to automatically turn to operate in the normal mode to detect the TAG signals of the target;

a signal processing module adapted to process the detected TAG signals and the detected rhythm and amplitude of the heartbeat of the target subject for determining relevant characteristic parameters and indexes of the TAG signals from the target subject;

wherein, when operated in the normal mode, the signal processing module is configured to process the TAG signals based on a statistical calculation; and wherein, when operated in the power saving mode, the signal processing module is configured to process the rhythm and amplitude of the heartbeat based on estimation from a mathematical model;

wherein the relevant characteristic parameters and indexes of the TAG signals comprise at least one of root mean square value of continuous blood pressure (RMSBP) and standard deviation of continuous blood pressure (SDBP);

wherein, when operated in the normal mode, the RMSBP is determined based on the statistical calculation using the detected TAG signals:

$$RMSBP = rmsv[tag(t)] = \sqrt{\frac{1}{N}\sum_{i=1}^{N}x_i^2}$$

where $x_i$ is a continuous blood pressure value, N is a number of data points, rmsv is a root mean square value, and tag is a continuous blood pressure signal;

wherein, when operated in the power saving mode, the RMSBP is determined based on the estimation from the mathematical model using the detected information on the rhythm and amplitude of the heartbeat:

$$RMSBP = \sqrt{\bar{a}^2\lambda h + d^2}$$

where $\bar{a}$ is an average pulse pressure within a predetermined monitoring period, $\lambda$ is an average heart rate within the predetermined monitoring period, $\lambda=E[1/(T_{i+1}-T_i)]$, $T_i$ , $T_{i+1}$ are random variables to indicate onset of blood pressure waveform per beat within the predetermined monitoring period, h is an average strength of the blood pressure waveform within the predetermined monitoring period, $$h = \int_{-\infty}^{\infty} h_{tag}^2(t)dt, \ h_{tag}(t)$$

is a continuous blood pressure waveform with a mean amplitude of 0 within one cardiac cycle, t indicates time, d is a predetermined constant represents for DC component of the blood pressure waveform, and E indicates a mean value of $[1/(T_{i+1}-T_i)]$;

wherein, when operated in the normal mode, the SDBP is determined based on the statistical calculation using the detected TAG signals:

$$SDBP = std[\text{tag}(t)] = \sqrt{\frac{1}{N-1}\sum_{i=1}^{N}|x_i - \mu|^2}$$

where $x_i$ is a continuous blood pressure value, N is a number of data points, $\mu$ is a mean of the continuous blood pressure value, and std is standard deviation, tag is a continuous blood pressure signal;

wherein, when operated in the power saving mode, the SDBP is determined based on the estimation from the mathematical model using the detected information on the rhythm and amplitude of the heartbeat:

$$SDBP = \bar{a}\sqrt{\lambda h}$$

where $\bar{a}$ is the average pulse pressure within a predetermined monitoring period, $\lambda$ is an average heart rate within predetermined monitoring period, $\lambda=E[1/(T_{i+1}-T_i)]$, $T_i$, $T_{i+1}$ are random variables to indicate the onset of blood pressure waveform per beat within the predetermined monitoring period, h is an average strength of the blood pressure waveform within the predetermined monitoring period $$h = \int_{-\infty}^{\infty} h_{tag}^2(t)dt, \ h_{tag}(t)$$

is a continuous blood pressure waveform with a mean amplitude of 0 within one cardiac cycle, t indicates time and E indicates the mean value of $[1/(T_{i+1}-T_i)]$;

an evaluation module for evaluating a status of a continuous blood pressure of the target subject based on the characteristic parameters and indexes obtained from the target subject; wherein the evaluation module is configured to determine a continuous blood pressure level based on the RMSBP, and to determine a continuous blood pressure variability based on the SDBP; and an alarm module for initiating an alarm when the relevant characteristic parameters and indexes of the TAG signals monitored are abnormal.

2. The apparatus according to claim 1, wherein the continuous blood pressure sensor comprises one or more of a multi-wavelength photoplethysmogram (PPG) sensor, a single-wavelength PPG sensor, an electrocardiogram (ECG) sensor, and a pressure sensor.

3. The apparatus according to claim 1, wherein based on the determined continuous blood pressure level, the evaluation module characterizes the overall blood pressure level of the target subject.

4. The apparatus according to claim 1, wherein based on the determined continuous blood pressure variability, the evaluation module characterizes the continuous blood pressure variability of the target subject.

5. The apparatus according to claim 1, wherein based on the obtained relevant characteristic parameters and indexes of TAG signals, the signal processing module characterizes any one of heart rate, pulse pressure, blood pressure waveform and vascular compliance of the target subject.

6. The apparatus according to claim 1, wherein based on the obtained relevant characteristic parameters and indexes of TAG signals, the signal processing module classifies the target subject, the classification of the target subject includes a hypertensive category.

7. The apparatus according to claim 1, wherein the alarm module has the forms of one or more of local alarm to call for help, sending an alarm message to an emergency contact of the target user and sending an alarm message to an emergency centre.

8. The apparatus according to claim 1, wherein the apparatus is implemented in a wearable, unobtrusive continuous blood pressure measurement device, forms of the device include one or more of a cell phone, a watch, a bracelet, a ring, a wristband, and a vest.

9. A method for detecting abnormality in blood pressure of a target subject for diagnosis of acute cardiovascular disease using the apparatus of claim 1, the method comprises:

via at least the continuous blood pressure sensor of the signal acquisition module, acquiring, tonoarteriogram (TAG) signals from the target subject when the signal acquisition module is operated in the normal mode, and acquiring the information on rhythm and amplitude of heartbeat of the target subject when the signal acquisition module is operated in the power saving mode;

wherein, when the change in the rhythm and amplitude of the heartbeat of the target subject is detected to exceed the predetermined threshold, switching from the power saving mode automatically to the normal mode to acquire the TAG signals of the target subject;

processing, via the signal processing module, the acquired TAG signals and the acquired rhythm and amplitude of the heartbeat of the target subject to determine relevant characteristic parameters and indexes of the TAG signals from the target subject;

wherein, when operated in the normal mode, the signal processing module is configured to process the TAG signals based on the statistical calculation; and wherein, when operated in the power saving mode, the signal processing module is configured to process the rhythm and amplitude of the heartbeat based on estimation from the mathematical model;

wherein the relevant characteristic parameters and indexes of the TAG signals comprise at least one of the RMSBP and the SDBP;

wherein, when operated in the normal mode, determining the RMSBP based on the statistical calculation using the acquired TAG signals:

$$RMSBP = rmsv[\text{tag}(t)] = \sqrt{\frac{1}{N}\sum_{i=1}^{N}x_i^2}$$

where $x_i$ is the continuous blood pressure value, N is the number of data points, rmsv is the root mean square value, and tag is the continuous blood pressure signal;

wherein, when operated in the power saving mode, determining the RMSBP based on the estimation from the mathematical model using the acquired information on the rhythm and amplitude of the heartbeat:

$$RMSBP = \sqrt{\overline{a}^2 \lambda h + d^2}$$

where $\overline{a}$ is the average pulse pressure within the predetermined monitoring period, $\lambda$ is the average heart rate within the predetermined monitoring period $\lambda = E[1/(T_{i+1} - T_i)]$, $T_i$, $T_{i+1}$ are random variables to indicate the onset of blood pressure waveform per beat within the predetermined monitoring period, h is the average strength of the blood pressure waveform within predetermined monitoring period $$h = \int_{-\infty}^{\infty} h_{tag}^2(t)dt, \; h_{tag}(t)$$

is the continuous blood pressure waveform with the mean amplitude of 0 within one cardiac cycle, t indicates time, d is the predetermined constant represents for DC component of the blood pressure waveform, and E indicates the mean value of $[1/(T_{i+1} - T_i)]$;

wherein, when operated in the normal mode, the SDBP is determined based on the statistical calculation using the acquired TAG signals:

$$SDBP = std[\text{tag}(t)] = \sqrt{\frac{1}{N-1} \sum_{i=1}^{N} |x_i - \mu|^2}$$

where $x_i$ is the continuous blood pressure value, N is the number of data points, $\mu$ is the mean of continuous blood pressure value, and std is the standard deviation, tag is the continuous blood pressure signal;

wherein, when operated in the power saving mode, the SDBP is determined based on the estimation from the mathematical model using the detected information on the rhythm and amplitude of the heartbeat:

$$SDBP = \overline{a}\sqrt{\lambda h}$$

where $\overline{a}$ is the average pulse pressure within the predetermined monitoring period, $\lambda$ is the average heart rate within predetermined monitoring period $\lambda = E[1/(T_{i+1} - T_i)]$, $T_i$, $T_{i+1}$ are random variables to indicate the onset of blood pressure waveform per beat within the predetermined monitoring period, h is the average strength of the blood pressure waveform within the predetermined monitoring period $$h = \int_{-\infty}^{\infty} h_{tag}^2(t)dt, \; h_{tag}(t)$$

is the continuous blood pressure waveform with the mean amplitude of 0 within one cardiac cycle, t indicates time and E indicates the mean value of $[1/(T_{i+1} - T_i)]$;

evaluating, via the evaluation module, the status of the continuous blood pressure of the target subject based on the characteristic parameters and indexes obtained from the target subject; wherein the evaluation module is configured to determine the continuous blood pressure level based on the RMSBP, and to determine the continuous blood pressure variability based on the SDBP; and initiating, via the alarm module, the alarm when the relevant characteristic parameters and indexes of the TAG signals monitored are abnormal.

10. The method according to claim 9, wherein the evaluating step comprises characterizing the overall blood pressure level of the target subject based on assessing the continuous blood pressure level and/or characterizing the continuous blood pressure variability of the target subject based on the assessed continuous blood pressure variability.

11. An electronic device for detecting abnormality in blood pressure of a target subject for diagnosis of acute cardiovascular disease, comprising:

a signal acquisition module comprises at least a continuous blood pressure sensor adapted to operate in a normal mode and a power saving mode, wherein the signal acquisition module detects tonoarteriogram (TAG) signals from a target subject in the normal mode, and detects information on rhythm and amplitude of heartbeat of the target subject in the power saving mode;

wherein, when a change in the rhythm and amplitude of the heartbeat of the target subject is detected to exceed a predetermined threshold when operated in the power saving mode, the signal acquisition module is adapted to automatically turn to operate in the normal mode to acquire the TAG signals of the target;

a signal processing module adapted to process the detected TAG signals and the detected rhythm and amplitude of the heartbeat of the target subject for obtaining relevant characteristic parameters and indexes of the TAG signals from the target subject;

wherein, when operated in the normal mode, the signal processing module is configured to process the TAG signals based on a statistical calculation; and wherein, when operated in the power saving mode, the signal processing module is configured to process the rhythm and amplitude of the heartbeat based on estimation from a mathematical model;

wherein the relevant characteristic parameters and indexes of the TAG signals comprise at least one of root mean square value of continuous blood pressure (RMSBP) and standard deviation of continuous blood pressure (SDBP);

wherein, when operated in the normal mode, the RMSBP is determined based on the statistical calculation using the detected TAG signals:

$$RMSBP = rmsv[\text{tag}(t)] = \sqrt{\frac{1}{N} \sum_{i=1}^{N} x_i^2}$$

where $x_i$ is a continuous blood pressure value, N is a number of data points, rmsv is a root mean square value, and tag is a continuous blood pressure signal;

wherein, when operated in the power saving mode, the RMSBP is determined based on the estimation from the mathematical model using the detected information on the rhythm and amplitude of the heartbeat:

$$RMSBP = \sqrt{\bar{a}^2 \lambda h + d^2}$$

where $\bar{a}$ is an average pulse pressure within a predetermined monitoring period, $\lambda$ is an average heart rate within the predetermined monitoring period, $\lambda = E[1/(T_{i+1}-T_i)]$, $T_i$, $T_{i+1}$ are random variables to indicate onset of blood pressure waveform per beat within the predetermined monitoring period, h is an average strength of the blood pressure waveform within the predetermined monitoring period, $$h = \int_{-\infty}^{\infty} h_{tag}^2(t)dt, \; h_{tag}(t)$$

is a continuous blood pressure waveform with a mean amplitude of 0 within one cardiac cycle, t indicates time, d is a predetermined constant represents for DC component of the blood pressure waveform, and E indicates a mean value of $[1/(T_{i+1}-T_i)]$;

wherein, when operated in the normal mode, the SDBP is determined based on the statistical calculation using the detected TAG signals:

$$SDBP = std[\text{tag}(t)] = \sqrt{\frac{1}{N-1}\sum_{i=1}^{N}|x_i - \mu|^2}$$

where $x_i$ is a continuous blood pressure value, N is a number of data points, $\mu$ is a mean of the continuous blood pressure value, and std is standard deviation, tag is a continuous blood pressure signal;

wherein, when operated in the power saving mode, the SDBP us determined based on the estimation from the mathematical model using the detected information on the rhythm and amplitude of the heartbeat:

$$SDBP = \bar{a}\sqrt{\lambda h}$$

where $\bar{a}$ is the average pulse pressure within a predetermined monitoring period, $\lambda$ is an average heart rate within predetermined monitoring period, $\lambda = E[1/(T_{i+1}-T_i)]$, $T_i$, $T_{i+1}$ are random variables to indicate the onset of blood pressure waveform per beat within the predetermined monitoring period, h is an average strength of the blood pressure waveform within the predetermined monitoring period $$h = \int_{-\infty}^{\infty} h_{tag}^2(t)dt, \; h_{tag}(t)$$

is a continuous blood pressure waveform with a mean amplitude of 0 within one cardiac cycle, t indicates time and E indicates the mean value of $[1/(T_{i+1}-T_i)]$;

an evaluation module for evaluating a status of a continuous blood pressure of the target subject based on the characteristic parameters and indexes obtained from the target subject; wherein the evaluation module is configured to determine a continuous blood pressure level based on the RMSBP, and to determine a continuous blood pressure variability based on the SDBP; and an alarm module for initiating an alarm when the relevant characteristic parameters and indexes of the TAG signals monitored are abnormal.

\* \* \* \* \*